(12) United States Patent
Higgins et al.

(10) Patent No.: US 9,956,243 B2
(45) Date of Patent: *May 1, 2018

(54) COMBINATION TREATMENT FOR ACUTE MYELOID LEUKEMIA (AML)

(71) Applicant: Hoffmann-La Roche Inc., Nutley, NJ (US)

(72) Inventors: Brian Higgins, Fresh Meadows, NY (US); Gwen Nichols, New York, NY (US); Kathryn E. Packman, Newton, MA (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 119 days.

This patent is subject to a terminal disclaimer.

(21) Appl. No.: 14/560,086

(22) Filed: Dec. 4, 2014

(65) Prior Publication Data

US 2015/0157603 A1 Jun. 11, 2015

Related U.S. Application Data

(60) Provisional application No. 61/912,152, filed on Dec. 5, 2013.

(51) Int. Cl.
| | | |
|---|---|---|
| *A01N 43/04* | (2006.01) | |
| *A61K 31/70* | (2006.01) | |
| *A61K 31/7068* | (2006.01) | |
| *A61K 9/00* | (2006.01) | |
| *A61K 31/40* | (2006.01) | |
| *A61K 45/06* | (2006.01) | |
| *A61K 31/77* | (2006.01) | |

(52) U.S. Cl.
CPC ........ *A61K 31/7068* (2013.01); *A61K 9/0019* (2013.01); *A61K 31/40* (2013.01); *A61K 31/77* (2013.01); *A61K 45/06* (2013.01)

(58) Field of Classification Search
CPC .. A61K 9/0019; A61K 31/40; A61K 31/7068; A61K 31/77; A61K 45/06; A61K 2300/00
See application file for complete search history.

(56) References Cited

U.S. PATENT DOCUMENTS

| 8,993,614 B2* | 3/2015 | Bartkovitz | C07F 9/5727 |
| | | | 514/359 |
| 2011/0251252 A1 | 10/2011 | Wang et al. | |
| 2011/0319378 A1 | 12/2011 | Bartberger et al. | |
| 2015/0211073 A1* | 7/2015 | Zhong | C12Q 1/6886 |
| | | | 514/254.05 |

FOREIGN PATENT DOCUMENTS

| DE | 102005012681 A1 | 9/2006 |
| WO | 2013135648 A1 | 9/2013 |

OTHER PUBLICATIONS

The English translation of the Taiwanese Office Action, dated Jul. 6, 2016, in the related Taiwanese patent application No. 103142020.
The English translation of the Taiwanese Search Report, dated Aug. 26, 2015, in the related Taiwanese patent application No. 103142020.
The International Search Report and Written Opinion, dated Feb. 10, 2015, in the related PCT Appl. No. PCT/EP2014/076063.
Anonymous: "NCT01773408 on Jul. 1, 2013: A Study of RO5503781 as Single Agent or in Combination With Cytarabine in Patients With Acute Myelogenous Leukemia", ClinicalTrials.gov Archive, Jul. 1, 2013(Jul. 1, 2013), Retrieved from the Internet: URL:https://clinicaltrials.gov/archive/NCT 01773408/2013_07 01.
Karin Yee: "Phase lb Study of the MDM2 1,8, Antagonist RG7112 in Combination With 2 10-12,20 Doses/Schedules of Cytarabine", Blood Journal 122(21), Nov. 15, 2013(Nov. 15, 2013), p. 498.
K. Kojima: "MDM2 antagonists induce 1,8, p53-dependent apoptosis in AML: implications for leukemia therapy", Blood, vol. 106, No. 9, Nov. 1, 2005(Nov. 1, 2005), pp. 3150-3159.
Ding et al: "Discovery of RG7388, a Potent and Selective p53-MDM2 Inhibitor in Clinical Development", Journal of Medicinal Chemistry, vol. 56, No. 14,Jul. 25, 2013(Jul. 25, 2013) 1-20, pp. 5979-5983.
Zak et al: "Mdm2 and MdmX inhibitors for the treatment of cancer: a patent review (2011-present)", Expert Opinion on Therapeutic Patents, vol. 23, No. 4, Apr. 1, 2013(Apr. 1, 2013), pp. 425-448.

* cited by examiner

*Primary Examiner* — Lawrence E Crane

(57) ABSTRACT

The present invention relates to a pharmaceutical product comprising a) as a first component an inhibitor of the MDM2-p53 interaction such as, for example:

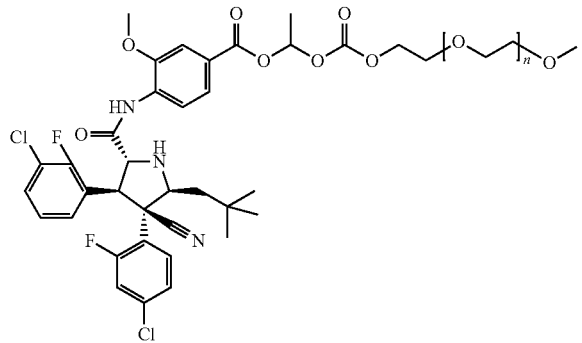

and b) as a second component cytarabine; as a combined preparation for the sequential or simultaneous use in the treatment of cancer.

13 Claims, 1 Drawing Sheet

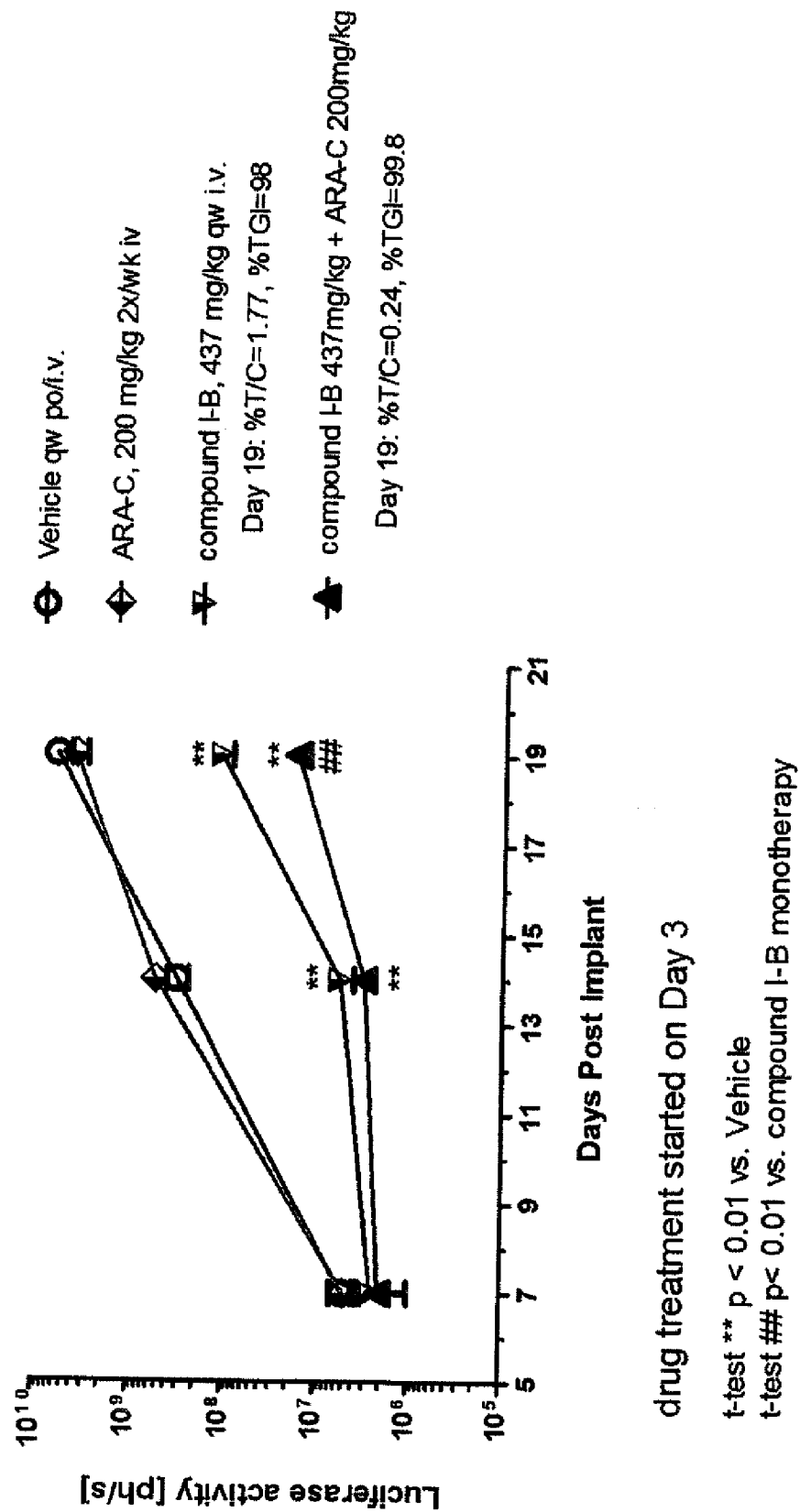

COMBINATION TREATMENT FOR ACUTE MYELOID LEUKEMIA (AML)

FIELD OF THE INVENTION

The present invention relates to a combination therapy for the treatment of proliferative disorders such as cancer, in particular Acute Myeloid Leukemia (AML). More particularly, the present invention discloses combinations of the current backbone therapy in AML, the compound cytarabine (Ara-C), together with a compound which acts as an inhibitor of the MDM2-p53 interaction. It was surprisingly found that such combinations show a more than additive (synergistic) effect.

BACKGROUND OF THE INVENTION p53 is a tumor suppressor protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 is dysregulated in many cancers. Frequently occurring molecular defects in the p16INK4/p19ARF locus, for instance, have been shown to affect MDM2 protein degradation. Inhibition of MDM2-p53 interaction in tumor cells with functional p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells with functional p53 signaling.

Inhibitors of the MDM2-p53 interaction have been shown to induce apoptosis in the established human AML cell line MOLM-13, which overexpresses MDM2 (K. Kojima, et. al., *Blood* 2005, 106(9):3150-9). It has now been found that the combination of compounds of formula (I) together with Ara-C provide more than additive effects in disseminated MOLM-13 AML model in immunocompromised mice.

Compounds of formula (I) and their preparation are disclosed in WO2013/135648. These compounds act as pro drugs of the compound

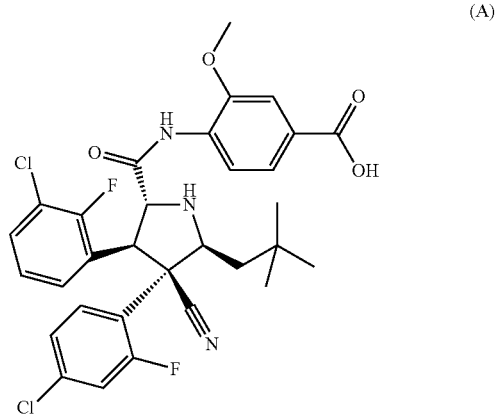

(A)

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (herein compound A).

Compound A is for example disclosed in U.S. Pat. No. 8,354,444 and WO2011/098398.

SUMMARY OF THE INVENTION

The present invention relates to a pharmaceutical product comprising a) as a first component an inhibitor of the MDM2-p53 interaction (also "MDM2 inhibitor"); and b) as a second component cytarabine; as a combined preparation for the sequential or simultaneous use in the treatment of cancer.

The present invention further relates to a method of treating a patient suffering from cancer, comprising administering to the patient the combination as mentioned above.

The present invention also relates to a kit comprising a) a first component which comprises, as an active agent, an inhibitor of the MDM2-p53 interaction; and b) a second component which comprises, as an active agent, the compound cytarabine.

In addition, the present invention relates to the use of an MDM2 inhibitor and cytarabine for the treatment of cancer.

A yet further aspect of the present invention is the use of an MDM2 inhibitor, and cytarabine for the preparation of a medicament for the treatment of cancer.

In one embodiment, the inhibitor of the MDM2-p53 interaction is selected from a compound of formula (I)

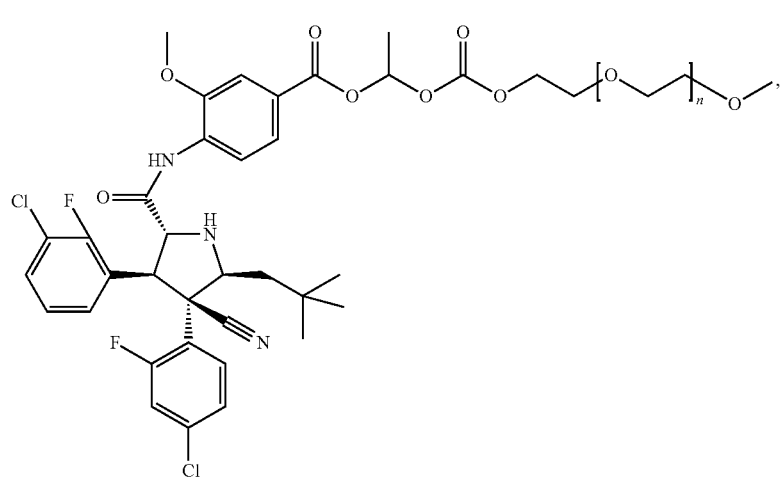

(I)

BRIEF DESCRIPTION OF THE DRAWINGS

FIG. 1 illustrates the antitumor efficacy of the compound I-B in combination with cytarabine on MOLM-13-luc.c4 (AML) tumor burden in SCID-beige mice, by quantification of bioluminescence.

DETAILED DESCRIPTION OF THE INVENTION

Compounds of formula (I), and in particular I-A and I-B as disclosed herein, are polyethylene glycol (PEG) prodrugs of compound (A) that were synthesized to provide the solubility required for an intravenous (iv) formulation of the active parent molecule compound (A). An iv formulation is desirable to ameliorate dose-limiting gastrointestinal intolerability and exposure variability, as well as to provide an acceptable route of administration for treatment of hematological malignancies and for pediatric use.

The anti-tumor activity of once weekly iv administration of compound I-B and oral (po) compound (A) were compared as monotherapies and in combination with the AML standard of care, cytarabine (Ara-C), in the MOLM-13 model. Both compounds I-B and (A) elicited a significant increase in lifespan (ILS) as monotherapies, with up to 37% ILS observed as compared to Vehicle control animals. Despite the lack of monotherapy activity with Ara-C, it did significantly prolong survival in combination with compound I-B or (A), with maximum ILS of 54% or 68% observed, respectively. The synergistic effect demonstrated by the present data suggests that the combination of targeting MDM2-p53 with an MDM2 inhibitor and inducing S-phase arrest with cytarabine (Ara-C) may be an effective therapeutic strategy for the treatment of AML. These data also demonstrate that the efficacy of compound (A) can be maintained by the prodrug approach using the compounds of formula (I), and in particular I-A and/or I-B.

Therefore, in one embodiment, the present invention relates to a pharmaceutical product comprising a) as a first component an inhibitor of the MDM2-p53 interaction; and b) as a second component cytarabine; as a combined preparation for the sequential or simultaneous use in the treatment of AML.

In another embodiment, the inhibitor of the MDM2-p53 interaction is selected from a compound of formula (I)

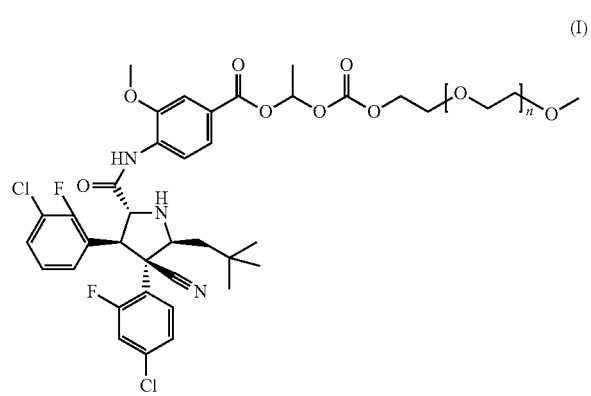

(I)

wherein n is from 3 to 70.

In one embodiment, n is from 30 to 60.

In another embodiment, n is from 40 to 50.

In yet another embodiment, n is 41, 42, 43, 44, 46, 47, 48 or 49.

In another embodiment the compound of formula (I) is: 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]amino}-3-methoxy-benzoic acid 1-mPEG-carbonyloxy-ethyl ester (mPEG, average MW, ~2000). This compound is designated herein as compound I-A.

In another embodiment the compound of formula (I) is: 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]amino}-3-methoxy-benzoic acid 1-mPEG-carbonyloxy-ethyl ester (mPEG, average MW, ~2200). This compound is designated herein as compound I-B.

In yet another embodiment, the MDM2 inhibitor according to the present invention may be the compound (A). Within this embodiment, compound (A) is preferably provided as preparation for peroral administration comprising an amorphous solid dispersion, preferably a micro precipitated bulk powder (MBP), comprising compound (A) and a polymer which stabilizes compound (A) in its amorphous form, preferably HPMCAS. The peroral preparation is reconstituted immediately before administration as a suspension in Klucel/Tween. Compound (A) can be prepared according to methods for example disclosed in U.S. Pat. No. 8,354,444 or WO2011/098398. Dose selection in the current studies was based on previously determined optimal doses for compound (A) in pre-clinical (animal) and clinical (phase 1) trials.

The pharmaceutical products or methods according to the present invention are particularly useful in the treatment or control of hematological tumors, such as leukemias, and especially for the treatment of Acute Myeloid Leukemia (AML). They may also be useful in the treatment of other cell proliferative disorders caused by disregulation of the MDM2-p53 interaction, such as cancer, more particularly solid tumors such as, for example, breast, colon, lung, melanoma, prostate, kidney, head and neck, or sarcoma.

In one embodiment the present invention provides the present pharmaceutical products and/or methods for the treatment of Acute Myeloid Leukemia (AML).

In another embodiment the present invention provides the present pharmaceutical products and/or methods for the treatment of cell proliferative disorders caused by disregulation of the MDM2-p53 interaction, such as cancer, more particularly solid tumors such as, for example, breast, colon, lung, melanoma, prostate, kidney, head and neck, or sarcoma.

Formulations of the compounds of formula (I) include those suitable for oral, nasal and/or parenteral or intravenous administration. The formulations may conveniently be presented in unit dosage form and may be prepared by any methods well known in the art of pharmacy.

In one embodiment, the compound of formula (I) is provided in a stable lyophilized formulation for intravenous administration comprising from about 0.1 mg to about 100 mg of compound (I), from about 10 mM to about 100 mM of a buffering agent, from about 25 mg to about 125 mg of a lyophilization bulking agent and an isotonicity builder. The resultant formulation should have a pH of about 5-7 via adjustment with HCl or NaOH.

In another embodiment, the compound of formula (I) is dissolved in 0.9% sodium chloride in sterile water by vortexing, then filtered thru a filter into a septum sealed vial for intravenous administration.

The term "buffering agent" as used herein denotes a pharmaceutically acceptable excipient, which stabilizes the pH of a pharmaceutical preparation. Suitable buffers are well known in the art and can be found in the literature. Preferred pharmaceutically acceptable buffers comprise but are not limited to histidine-buffers, citrate-buffers, succinate-buffers, acetate-buffers and phosphate-buffers, especially, Succinic acid (20-50 mM) and Phosphoric acid (10-50 mM). Most preferred buffers comprise citrate, L-histidine or mixtures of L-histidine and L-histidine hydrochloride. Other preferred buffer is acetate buffer. Independently from the buffer used, the pH can be adjusted with an acid or a base known in the art, e.g. hydrochloric acid, acetic acid, phosphoric acid, sulfuric acid and citric acid, sodium hydroxide and potassium hydroxide.

The preferred "bulking agent" is Trehalose dihydrate but lactose, sucrose, sorbitol, glucose, raffinose, mannitol, dextran and lower molecular weight amino acids such as glycine, valine and arginine etc. and other bulking agents described in the scientific literature may also be utilized.

As diluents for the formulated solution or reconstituted solution from the lyophilized powder the following diluents such as sodium chloride (0.9%), 5% Dextrose, water for injection, Lactated Ringers solution or half normal saline may also be used. It is to be appreciated that the bulking agent may also act as the isotonicity building agent.

The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent. A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005.

Cytarabine was purchased from Hospira, Inc. Lake Forest, Ill. 60045 USA, as sterile solution (100 mg/ml) for intravenous (iv) injection.

The compounds of formula (I) as well as cytarabine are administered in their therapeutically effective amount. More particularly, the compounds of formula (I), especially of formula I-A and I-B, are dosed in order to deliver a therapeutically active amount of compound A to a patient. A therapeutically effective amount of a compound in accordance with this invention means an amount of compound that is effective to prevent, alleviate or ameliorate symptoms of disease or prolong the survival of the subject being treated. The determination of the amount of a pro drug, for example a compound of formula (I), such as I-A or I-B, in order to deliver a desired amount of active principal, for example the compound A, to a patient is within routine work of a person of ordinary skill in pharmaceutical sciences. In one embodiment of the present invention the dose of prodrug of formula I-B of 437 mg/kg is equivalent to 100 mg/kg of parent MDM2 inhibitor of compound (A), due to 22.88% active compound loading in the prodrug.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 3,000 mg, preferably from about 80 mg to about 1600 mg of compound (A), should be appropriate, although the upper limit may be exceeded when indicated. The daily dosage can be administered as a single dose or in divided doses, or for parenteral administration; it may be given as continuous infusion.

In one embodiment, the present pharmaceutical products comprise compounds of formula (I) characterized in that they are dosed in such way as to deliver compound (A) in an amount of from about 50 to about 3000 mg/day, or from about 80 to about 2500 mg/day, or from about 80 to about 1600 mg/day, or from about 200 to about 1600 mg/day, or from about 400 to about 1600 mg/day, or from about 400 to about 1200 mg/day, or from about 400 to about 1000 mg/day, or from about 400 to about 800 mg/day, or from about 400 to about 600 mg/day for an administration period of up to about 7 days, preferably up to about 5 days, on days 1-7, or preferably days 1-5, of a 28 day treatment cycle, followed by a rest period of from about 21 to about 23 days, preferably up to about 23 days. The daily dosage, i.e. the amount of compound (A) expressed in mg/day, can be administered as a single dose (qd) or in two doses (BID). When two doses are given, they are preferably administered in equal amounts, once in the morning and once in the afternoon.

In another embodiment, the present pharmaceutical products comprise compounds of formula (I), I-A or I-B, characterized in that they are dosed in such way as to deliver compound A in an amount of from about 400 to about 1200 mg/day for an administration period of up to 5 days, on days 1-5, of a 28 day treatment cycle, followed by a rest period of 23 days. Within this embodiment, compound I-B is preferred.

A therapeutically effective amount (or "effective amount") of cytarabine in accordance with this invention means an amount effective to achieve the synergistic, i.e. more than additive effect as demonstrated by the data disclosed herein (see e.g. FIG. 1). Since cytarabine is used as the backbone therapy for AML for many years, a lot of information is available to the person of skill in the art, for example a clinical physician, about effective and tolerated doses in humans. It has for example been found that cytarabine can be dosed as single agent in the treatment of AML (induction regimen) in high amounts, such as amounts up to 3 g/m$^2$ (intravenous) over 2 hours every 12 hours days 1 to 6. A review about the use of cytarabine in the treatment of leukemias is for example provided in "Nicholas D. Reese, Gary J. Schiller; *Curr Hematol Malig Rep*, 2013, 8:141-148." In certain combination therapies (e.g. induction therapy of acute non-lymphocytic leukemia), the usual cytarabine dose in combination with other anti-cancer drugs is 100 mg/m$^2$/day by continuous iv infusion (Days 1-7) or 100 mg/m$^2$ iv every 12 hours (Days 1-7). (see for example www.hospira.com).

Therefore, in one embodiment the present invention provides a pharmaceutical product comprising, a) as an MDM2 inhibitor, a compound of formula (I), I-A or I-B, wherein said compound is administered intravenously (iv) once or two times per day on days 1 to 5, followed by a 23 days rest period, of a 28 days treatment cycle; and b) as a second component an effective amount of the compound cytarabine; as a combined preparation for the simultaneous or sequential treatment of cancer, preferably AML. Within this embodiment compounds I-A and I-B are preferred and are dosed in such way as to deliver compound (A) in an amount of from about 50 to about 3000 mg/day, or from about 80 to about 2500 mg/day, or from about 80 to about 1600 mg/day, or from about 200 to about 1600 mg/day, or from about 400 to about 1600 mg/day, or from about 400 to about 1200 mg/day, or from about 400 to about 1000 mg/day, or from about 400 to about 800 mg/day, or from about 400 to about 600 mg/day.

In a preferred embodiment, compound I-B is dosed two times a day (BID) as 600 mg doses in order to deliver a total daily dose of about 1200 mg of compound (A) to the patient.

In yet another embodiment, the present invention provides a method for the treatment of cancer, comprising administering to a patient in need of such treatment a pharmaceutical product as defined hereinbefore. Within this embodiment, the MDM2 inhibitor is preferably selected from compound I-A of I-B. Dosage forms, dosages and treatment schedules for compounds I-A or I-B and cytarabine are preferably as described above. Also, within this embodiment the cancer is a solid- or non-solid tumor, preferably the cancer is Acute Myeloid Leukemia (AML).

In another embodiment, the present invention provides the use of a compound of formula (I), preferably I-A or I-B, and cytarabine for the manufacture of a medicament for the treatment of cancer, in particular Acute Myeloid Leukemia (AML).

In another embodiment, the present invention provides a pharmaceutical product comprising, a) as a first component a compound of formula (I); and b) as a second component the compound cytarabine, both administered iv once or twice a day, as a combined preparation for the simultaneous or sequential use in the treatment of cancer; characterized in that the dose of the compound of formula (I) corresponds to a dose of compound (A) within the range from about 50 to about 3000 mg/day, or from about 80 to about 2500 mg/day, or from about 80 to about 1600 mg/day, or from about 200 to about 1600 mg/day, or from about 400 to about 1600 mg/day, or from about 400 to about 1200 mg/day, or from about 400 to about 1000 mg/day, or from about 400 to about 800 mg/day, or from about 400 to about 600 mg/day. Within this embodiment, the compound of formula (I) preferably is the compound I-A or I-B, the cancer is AML, the daily dose is from about 200 to about 1600 mg given once or twice a day, and the dosage regimen for the compounds I-A or I-B is on day 1 to 5, followed by a 23 days rest period of a 28 days treatment cycle. More preferably, within this embodiment, the compound of formula (I) is the compound I-B, the cancer is AML, the daily dose is about 1200 mg given once or twice (BID, 600 mg) a day on day 1 to 5, followed by a 23 days rest period of a 28 days treatment cycle.

The invention is now further illustrated by the following accompanying working Example.

Example

Materials and Methods

Animals

Female SCID beige mice (10/group), obtained from Charles River Laboratories (Wilmington, Del.) were used when they were approximately 8-12 weeks old and weighed approximately 20-25 grams. The health of the mice was assessed daily by gross observation and analyses of blood samples taken from sentinel animals housed on shared shelf racks. All animals were allowed to acclimate and recover from any shipping-related stress for a minimum of 72 hours prior to experimental use. Autoclaved water and irradiated food (5058-ms Pico Lab mouse chow, Purina Mills, Richmond, Ind.) were provided ad libitum, and the animals were maintained on a 12 hour light and dark cycle. Cages, bedding and water bottles were autoclaved before use and changed weekly. All animal experiments were conducted in accordance with the Guide for the Care and Use of Laboratory Animals, local regulations, and protocols approved by the Roche Animal Care and Use Committee in an AAALAC accredited facility.

Tumors

Parental MOLM-13 human AML cells were stably transfected with Luc2 lentiviral particles for 24 hrs in the presence of Polybrene (8 ug/ml) and then selected in the presence of Blasticidin for 3 weeks. Subsequently, one clone was selected by single cell plating in the presence of 0.1 mg/mL G418 and was designated MOLM-13.luc.c4. The lentiviral Luc2 expression plasmid was constructed by incorporating Luc2 gene (Promega) in to pLOC lentiviral plasmid backbone (Thermo Fisher Scientific). Luc2 lentiviral particles were prepared by using Trans-Lentiviral Packaging System (Thermo Fisher Scientific) as recommended.

MOLM-13.luc.c4 was maintained with RPMI 1640 with L-glutamine (2 mM) media (GIBCO/Invitrogen, Carlsbad, Calif.) supplemented with 10% heat-inactivated Fetal Bovine Serum (HI-FBS; GIBCO/Invitrogen, Carlsbad, Calif.), and 1% 100 mM sodium pyruvate. Freshly dissociated MOLM13-Luc.c4 cells (1×106 or 5×106) suspended in Phosphate Buffered Saline (PBS) were then intravenously inoculated via the caudal tail vein into female SCID-beige mice.

Test Agent

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2200), i.e. compound I-B, was dissolved in 0.9% sodium chloride in sterile water by vortexing. It was then filtered thru a 0.22 micron filter into a septum sealed vial for intravenous administration. Dose of the drug of 437 mg/kg is equivalent to 100 mg/kg of parent MDM2 inhibitor due to 22.88% active compound loading in the prodrug. Stock cytarabine (Ara-C injection, 100 mg/ml) was diluted in sterile 0.9% sodium chloride to 44 mg/ml according to manufacturer's instructions and dosed at 200 mg/kg iv twice weekly.

Compound I-B and cytarabine were administered iv using a 1 cc syringe and 26-gauge needle at 437 mg/kg (9 ml/kg) weekly (q7d) and 200 mg/kg (4.5 ml/kg) bi-weekly (2×/week), respectively. On days of concomitant administration, compound I-B was dosed in the morning and cytarabine was administered 6 hours later in compliance with IACUC regulations for intravenous volume administration. Treatment duration was 3 weeks.

Monitoring

For increased life span (ILS) assessment, animal body weights were measured two to three times per week, and animals were monitored daily for any clinical signs of toxicity or excessive tumor burden (i.e. hind limb paralysis or morbidity). In addition, progression of disease was monitored by in vivo bioluminescent imaging (BLI) using IVIS® Spectrum system. For each BLI session, mice received 100 mg/kg D-luciferin (Caliper Life Sciences/Perkin-Elmer) via ip injections and were imaged at 20 min post luciferin injection at either a 5 s or a 10 s exposure time. Images were captured by the IVIS® Spectrum system and data were collected and analyzed with Living Image 4.2.0 software (Caliper Life Sciences, Hopkinton, Mass.). Total photon fluxes (ph/s) representing luciferase activity within each fixed region of interest (ROI) covering whole tumors of individual mice were determined. The actual images of mice are not disclosed herein. Data for quantification of bioluminescence originated from this monitoring are provided in FIG. 1.

Calculations & Statistical Analysis

Weight loss was graphically represented as percent change in mean group body weight, using the formula: $((W-W_0)/W_0) \times 100$, where 'W' represents mean body weight of the treated group at a particular day, and '$W_0$' represents mean body weight of the same treated group at initiation of treatment. Maximum weight loss was also represented using the above formula, and indicated the maximum percent body weight loss that was observed at any time during the entire experiment for a particular group. Toxicity is defined as ≥20% of mice in a given group demonstrating ≥20% body weight loss and/or death.

Quantification of bioluminescence allowed for direct longitudinal comparison of tumor burden between treatment groups prior to surrogate death end points being reached. Tumor burden was graphically represented as the mean BLI photon flux+standard error of the mean (SEM), and median survival was determined utilizing Kaplan Meier survival analysis. Statistical analysis of comparisons between groups was analyzed by two-way ANOVA, and post-hoc Bonferroni test (GraphPad Prism, version 4.3). Differences between groups were considered to be significant when the probability value (p) was ≤0.05.

For survival assessment, morbidity or hind limb paralyses were monitored as end points and results were plotted as the percentage survival against days after tumor implant (GraphPad Prism, version 4.3). Hind limb paralysis, morbidity or ≥20% body weight loss were used as surrogates for death. The % ILS was calculated as 100×[(median survival day of treated group−median survival day of control group)/median survival day of control group]. Median survival was determined utilizing Kaplan Meier survival analysis. Survival in treated groups was compared with the vehicle group by Log-rank (Mantel-Cox) Test (GraphPad Prism, version 4.3). Differences between groups were considered significant when the probability value (p) was ≤0.05.

Results

Toxicity

Toxicity as assessed by animal body weight loss or gross clinical signs was not observed in the current studies. There were however, sporadic deaths directly after iv dosing of compound I-B of undetermined cause (potentially technical, though unproven, see Table 1).

TABLE 1

Summary of Toxicity data

| Group | Frequency | Route | % Change in Body Weight at Day 17 | # of animals ≥20% body weight loss | Mortality | Reason for Mortality/Morbidity |
|---|---|---|---|---|---|---|
| Vehicle Control | q7d + 2x/wk | iv + iv | −4.9 | 0 | 0 | N/A |
| compound I-B 437 mg/kg | q7d | iv | −2.8 | 0 | 1 | Undetermined |
| Ara-C 200 mg/kg | 2x/week | iv | −5.8 | 0 | 0 | N/A |
| compound I-B 437 mg/kg + Ara-C 200 mg/kg | q7d + 2x/week | iv + iv | −6.1 | 0 | 2 | Undetermined |

Antitumor Efficacy and Assessment of Survival/Increase in Life Span (ILS)

Mice were inoculated with 5 million cells and drug treatment was initiated on day 3. BLI demonstrated significantly reduced photon counts for mice receiving compound I-B monotherapy, whereas cytarabine (Ara-C) by itself showed no difference compared to Vehicle-treated control mice (see FIG. 1). These apparent reductions in tumor burden as assessed by BLI did translate into significant increases in lifespan, with 37% ILS observed for groups treated with q7d 437 mg/kg compound I-B. Cytarabine (Ara-C) demonstrated a lack of antitumor activity as assessed by tumor burden (BLI) or ILS. On the other hand, combinations with Ara-C and compound I-B elicited statistically significant % ILS as compared with Vehicle control or monotherapy arm, demonstrating a clear enhancement of antitumor activity in combination. These data are summarized in Table 2 below, also including a comparison with orally administered compound (A).

TABLE 2

Summary of Efficacy data

| Group | Vehicle Control | Cpd I-B 437 mg/kg q7d iv | Cpd (A) 100 mg/kg q7d po | Cpd (A) 80 mg/kg qd × 5 po | Ara-C 200 mg/kg 2x/wk iv | Cpd I-B 437 mg/kg + Ara-C 200 mg/kg | Cpd (A) 100 mg/kg + Ara-C 200 mg/kg | Cpd (A) 80 mg/kg + Ara-C 200 mg/kg |
|---|---|---|---|---|---|---|---|---|
| Median survival (days) | 20.5 | 28 | 25 | 28 | 20 | 31.5 | 26 | 34.5 |
| % ILS vs. Vehicle control | — | *37 | *22 | *37 | 0 | *†54 | *†27 | *†68 |

*p < 0.05 Vs. Vehicle Control
†p < 0.05 Vs. Monotherapy Arms
Cpd = compound

What is claimed:

1. A pharmaceutical product, comprising a) as a first component an inhibitor of the MDM2-p53 interaction; and b) as a second component cytarabine, wherein the inhibitor of the MDM2-p53 interaction is a compound of formula (I):

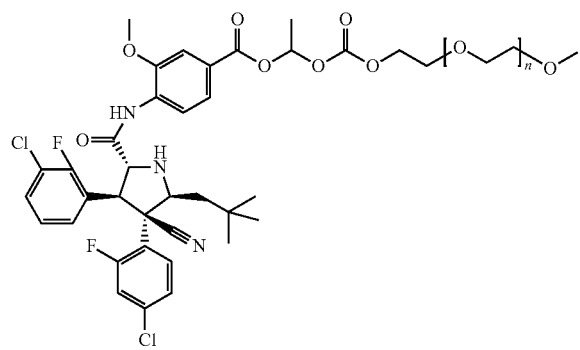

(I)

wherein n is from 3 to 70; or a compound of formula (A):

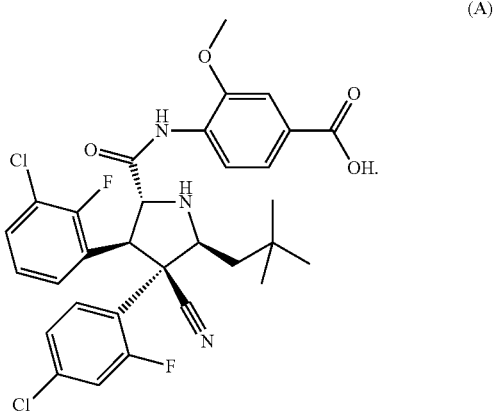 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

(A)

2. The pharmaceutical product according to claim 1, wherein n is from 30 to 60.

3. A method for treating acute myeloid leukemia, said method comprising: administering to a patient in need thereof the product of claim 2.

4. The pharmaceutical product according to claim 1, wherein a is from 40 to 50.

5. A method for treating acute myeloid leukemia, said method comprising: administering to a patient in need thereof the product of claim 4.

6. The pharmaceutical product according to claim 1, wherein n is 41, 42, 43, 44, 46, 47, 48 or 49.

7. A method for treating acute myeloid leukemia, said method comprising: administering to a patient in need thereof the product of claim 6.

8. The pharmaceutical product according to claim 1, wherein the inhibitor of the MDM2-p53 interaction is 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000); or wherein the inhibitor of the MDM2-p53 interaction is 4-{[(2R,3S,4R,5S)-3-(3-chloro-2-fluoro-phenyl)-4-(4-chloro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2200); or combinations thereof.

9. A method for treating acute myeloid leukemia, said method comprising: administering to a patient in need thereof the product of claim 8.

10. The pharmaceutical product according to claim 1, wherein the inhibitor of the MDM2-p53 interaction is the compound of formula (A)

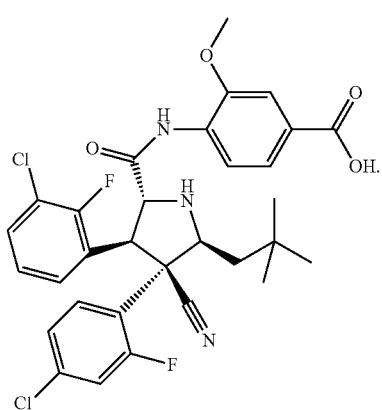

(A)

11. A method for treating acute myeloid leukemia, said method comprising: administering to a patient in need thereof the product of claim 1.

12. A pharmaceutical product, comprising, a) as a first component a compound of formula (I):

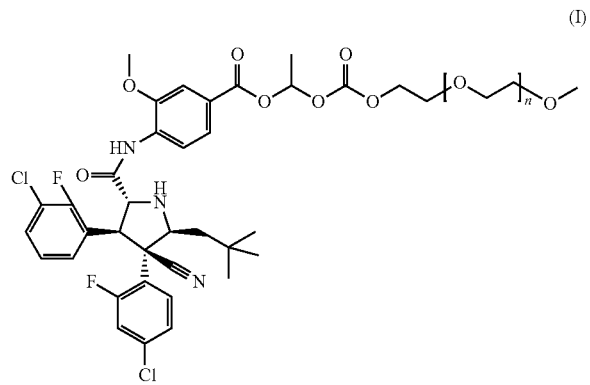

(I)

wherein n is from 3 to 70; and b) as a second component the compound cytarabine, wherein the dose of the compound of formula (I) corresponds to a dose of compound (A):

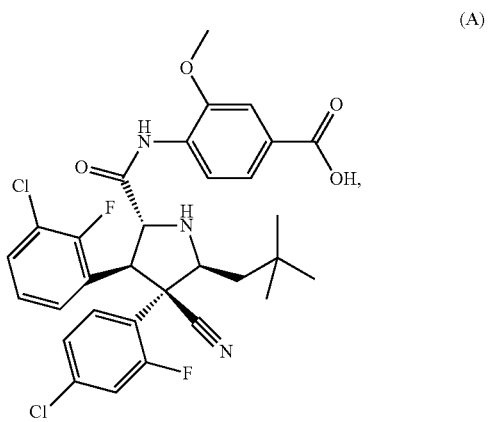 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

(A)

within the range from about 200 to about 1600 mg/day.

13. The pharmaceutical product according to claim 12, wherein the compound of formula (I) is the compound 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2000); or 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-methoxy-benzoic acid 1-mPEG-carbonyloxy-ethyl ester (mPEG, average MW, ~2200); or combinations thereof.

* * * * *

UNITED STATES PATENT AND TRADEMARK OFFICE
CERTIFICATE OF CORRECTION

PATENT NO. : 9,956,243 B2  
APPLICATION NO. : 14/560086  
DATED : May 1, 2018  
INVENTOR(S) : Brian Higgins, Gwen Nichols and Kathryn E. Packman Page 1 of 1

It is certified that error appears in the above-identified patent and that said Letters Patent is hereby corrected as shown below:

In the Claims

At Column 12, Line 46, Claim 4, "wherein a..." should be replaced with "wherein n..."

At Column 12, Line 64, Claim 8, "4-(4-chloro-phenyl)..." should be replaced with "4-(4-chloro-2-fluoro-phenyl)..."

Signed and Sealed this
Nineteenth Day of June, 2018

Andrei Iancu
*Director of the United States Patent and Trademark Office*